(12) United States Patent
Simopoulos et al.

(10) Patent No.: US 7,645,236 B2
(45) Date of Patent: Jan. 12, 2010

(54) ULTRASOUND IMAGING SYSTEM HAVING MOTION ADAPTIVE GAIN

(75) Inventors: Constantine Simopoulos, Menlo Park, CA (US); Bhaskar Ramamurthy, Los Altos, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 739 days.

(21) Appl. No.: 11/170,006

(22) Filed: Jun. 28, 2005

(65) Prior Publication Data

US 2007/0016024 A1 Jan. 18, 2007

(51) Int. Cl.
*A61B 8/00* (2006.01)

(52) U.S. Cl. .......................... 600/437; 73/631

(58) Field of Classification Search ................ 600/438, 600/440, 441, 444, 446, 453
See application file for complete search history.

(56) References Cited

U.S. PATENT DOCUMENTS

| | | | |
|---|---|---|---|
| 5,579,768 A * | 12/1996 | Klesenski | .................... 600/442 |
| 5,709,210 A | 1/1998 | Green et al. | |
| 5,788,635 A | 8/1998 | Wright et al. | |
| 5,833,614 A | 11/1998 | Dodd et al. | |
| 5,846,202 A | 12/1998 | Ramamurthy et al. | |
| 5,871,447 A | 2/1999 | Ramamurthy et al. | |
| 5,873,830 A | 2/1999 | Hossack et al. | |
| 5,882,306 A | 3/1999 | Ramamurthy et al. | |
| 5,913,823 A | 6/1999 | Hedberg et al. | |
| 5,961,460 A | 10/1999 | Guracar et al. | |
| 6,015,384 A | 1/2000 | Ramamurthy et al. | |
| 6,102,859 A * | 8/2000 | Mo | ........................... 600/443 |
| 6,132,377 A | 10/2000 | Bolorforosh et al. | |
| 6,174,286 B1 | 1/2001 | Ramamurthy et al. | |
| 6,193,659 B1 | 2/2001 | Ramamurthy et al. | |
| 6,221,018 B1 | 4/2001 | Ramamurthy et al. | |
| 6,398,733 B1 | 6/2002 | Simopoulos et al. | |
| 6,537,218 B1 | 3/2003 | Simopoulos et al. | |
| 6,579,238 B1 | 6/2003 | Simopoulos et al. | |
| 6,733,454 B1 | 5/2004 | Bakircioglu et al. | |
| 6,775,400 B1 | 8/2004 | Zhao et al. | |
| 2004/0073116 A1 * | 4/2004 | Smith | ......................... 600/450 |

\* cited by examiner

*Primary Examiner*—Long V Le
*Assistant Examiner*—Saurel J Selkin

(57) ABSTRACT

Disclosed are an apparatus and method of adjusting gain of an ultrasound system 100. In particular, subject matter is disclosed for receiving an indication 102 of a rate of change in motion of an object 106, and adjusting a gain based 108, at least in part, on said rate of change in motion, where the gain is adjusted at least partially corresponding to the rate of change in motion of the object 106.

30 Claims, 6 Drawing Sheets

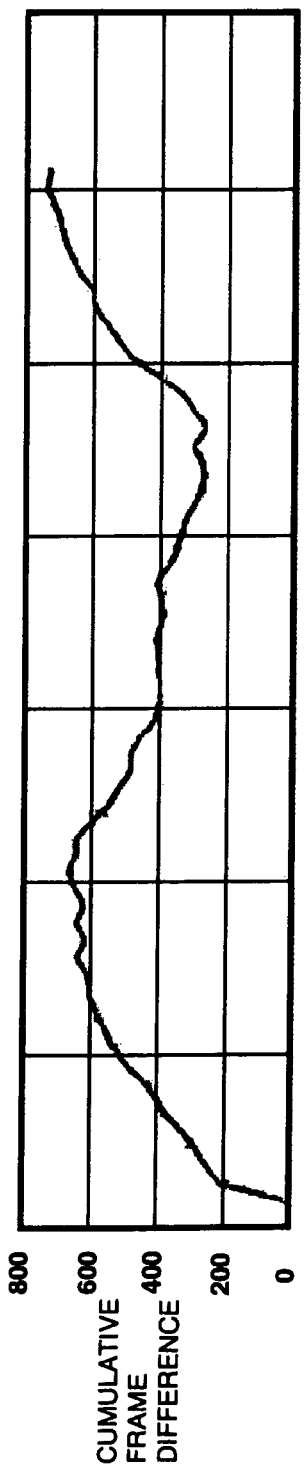
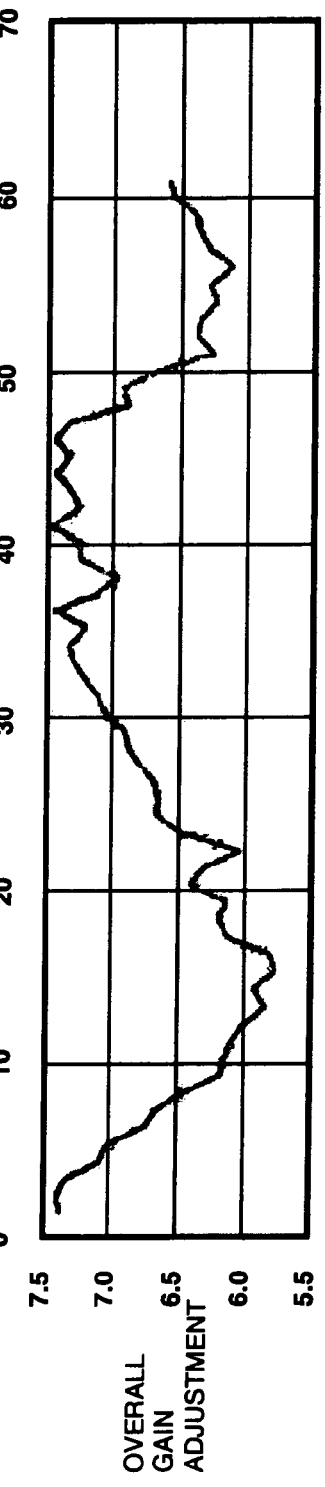
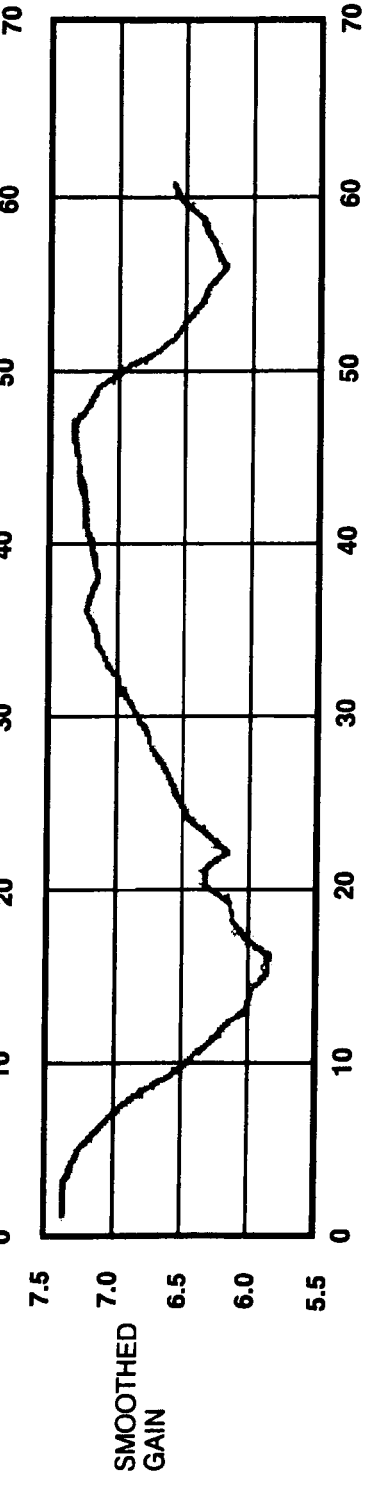
FIGURE 5A
FIGURE 5B
FIGURE 5C

ULTRASOUND IMAGING SYSTEM HAVING MOTION ADAPTIVE GAIN

BACKGROUND

1. Technical Field

The subject matter disclosed herein relates to ultrasonic imaging systems.

2. Information

"Imaging" refers to a process of capturing visual features of one or more objects of interest. "Ultrasound imaging" refers to a process of imaging which comprises the processing of acoustic signals, such as those reflected back by or transmitted through the one or more objects of interest. Medical professionals using ultrasound imaging technology typically employ images for diagnostic purposes.

In a typical ultrasound imaging system, an ultrasound image is formed from transmitting an acoustic signal, in the form of an ultrasonic waveform, through tissue and processing resulting reflections and/or transmissions of the acoustic signal from an object of interest. An example of a device for receiving the acoustic signal may comprise a transducer. The transducer typically receives acoustic signals and converts the acoustic signals into electrical signals for processing. The acoustic signals may vary considerably based at least in part on distance of travel from an object of interest and/or depth of travel through various tissue for example.

BRIEF DESCRIPTION OF THE DRAWINGS

Embodiments are illustrated by way of example and not by way of limitation in the figures of the accompanying drawings, in which like references may indicate similar elements and in which:

FIGS. 5A-5C are graphical representations illustrating at least one example, without limitations, of an adjustment of gain based, at least in part, on a rate of change in motion, where the gain is adjusted at least partially corresponding to the rate of change in motion of an object for one embodiment.

DETAILED DESCRIPTION

In the following description, embodiments will be disclosed. For purposes of explanation, specific numbers, materials, and/or configurations are set forth in order to provide a thorough understanding of the embodiments. However, it will also be apparent to one skilled in the art that the embodiments may be practiced without one or more of the specific details, or with other methods, materials, components, etc. In other instances, well-known structures, materials, and/or operations are not shown and/or described in detail to avoid obscuring the embodiments. Accordingly, in some instances, features are omitted and/or simplified in order to not obscure the disclosed embodiments. Furthermore, it is understood that the embodiments shown in the figures are illustrative representations and are not necessarily drawn to scale.

References throughout this specification to "one embodiment" or "an embodiment" means that a particular feature, structure, material, and/or characteristic described in connection with the embodiment is included in at least one embodiment. Thus, the appearances of the phrases "in one embodiment" and/or "in an embodiment" in various places throughout this specification are not necessarily all referring to the same embodiment. Furthermore, the particular features, structures, materials, and/or characteristics may be combined in any suitable manner in one or more embodiments.

In an ultrasound system, some examples of common imaging modes may comprise gray scale, Doppler, and/or venous/arterial mode. In general, gray scale mode utilizes bursts of acoustic signals, Doppler mode utilizes frequency shift principles, and venous/arterial mode utilizes both the gray scale mode and the Doppler mode.

Depending at least in part on the particular situation, an object of interest may not necessarily be stationary or rhythmically in motion, but instead, may change position at least partially erratically (e.g., movement of a fetus), which may have an effect image quality. Furthermore, a technician may move the transducer to a new location for imaging another object of interest, which may also have an effect on image quality. That is, an erratic or sudden change in acoustic signals might make it difficult to improve and/or optimize image quality for example. Accordingly, changes in acoustic signals, e.g., motion, may have an effect on the resulting images.

Figure 1:
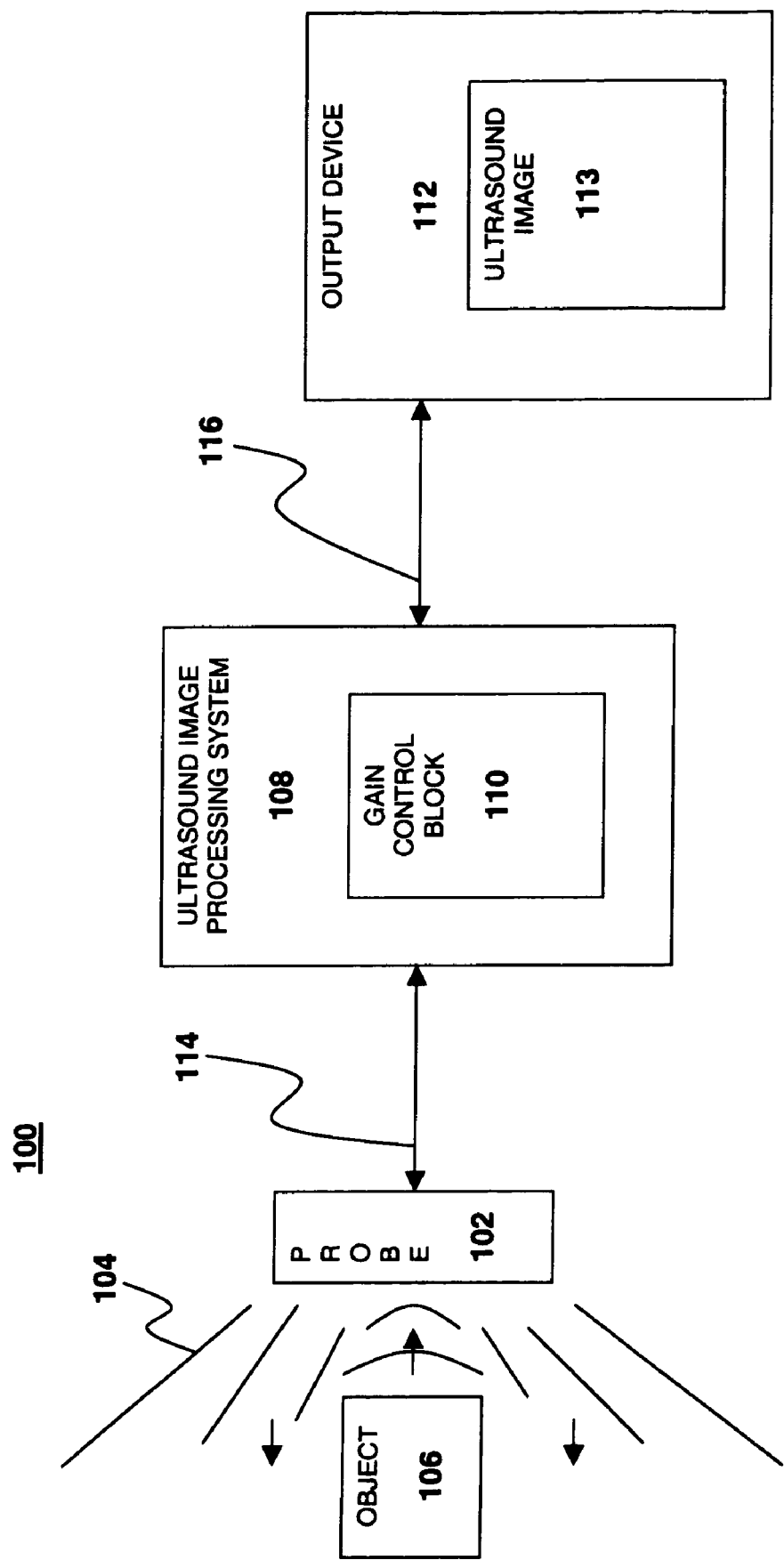
FIG. 1 is a schematic diagram of one embodiment of a diagnostic ultrasound imaging system.

Turning now to the figures, FIG. 1 is a schematic diagram of an embodiment of a diagnostic ultrasound imaging system. Ultrasound imaging system 100 may include various components, such as a probe 102 capable of transmitting and receiving an ultrasound image signal 104. In this embodiment, probe 102 may be directed towards an object 106 for diagnostic purposes. Additionally, probe 102 may be coupled to an ultrasound image processing system 108. In this embodiment, ultrasound image processing system 108, in particular, includes a gain control block 110. In turn, ultrasound image processing system 108 may be coupled to an output device 112, where an ultrasound image 113 may be displayed.

In FIG. 1, for the purposes here of describing an embodiment, object 106 may comprise an object that is located behind various tissue layers and subject to erratic motion, such as, but not limited to, a fetus. Probe 102 may comprise any type of probe capable of converting various types of measurable signal information into other signal forms, for example, a single transducer element or a number of individual transducer elements may be dispersed over a surface area forming a phased array, in which, the transducer elements are independently capable of transmitting a portion of an ultrasound image signal and receiving a portion of a received ultrasound image signal. In the illustrated embodiment of FIG. 1, probe 102 may be configured to "actively scan" the object 106 by transmitting ultrasound image signal 104 to object 106. Thus, in this particular embodiment, the probe 102 may receive energy from the object 106 (e.g., reflected ultrasound imaging signal 104). Accordingly, probe 102 may include piezoelectric materials to facilitate production of and reception of ultrasound image signal 104 for example. However, these are merely examples of a probe and claimed subject matter is not limited in scope in these respects.

Continuing to refer to FIG. 1, output device 112 may comprise any type of output device such as, but not limited to, a display device for displaying an ultrasound image, an audio device for transmitting sound, etc. Furthermore, output device 112 may comprise of any type of device including devices for receiving and storing data. As will be described in further detail, output device 112 may provide ultrasound image 113 to a viewer (not shown) representative of object 106.

Figure 2:
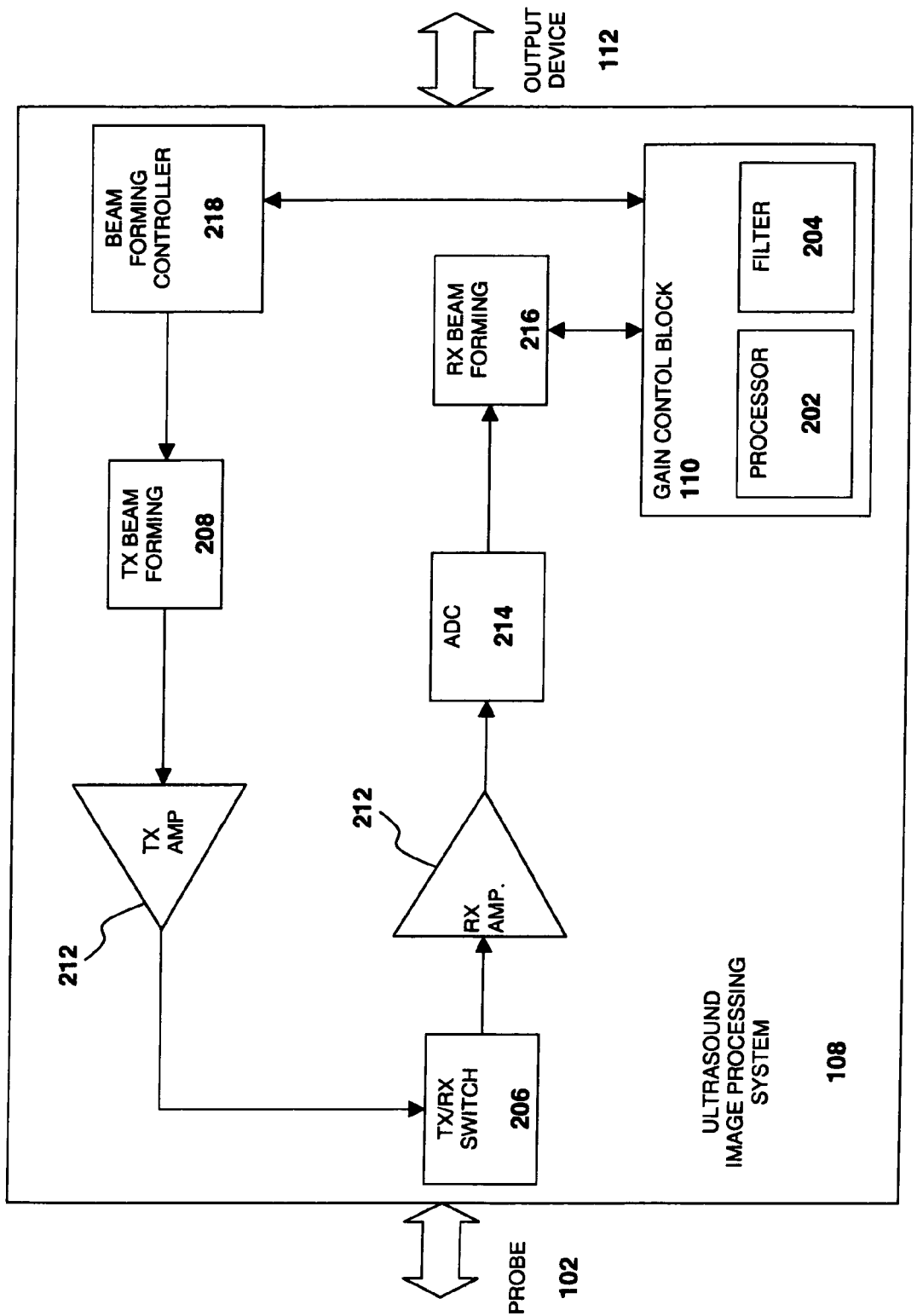
FIG. 2 illustrates the embodiment of FIG. 1 in greater detail.

FIG. 2 illustrates the embodiment of FIG. 1 in further detail. Briefly referring to FIG. 2, gain control block 110 may include various components for adjusting gain so as to affect quality of ultrasound image 113 based, at least in part, for example, on a rate of change in motion of object 106. As illustrated in FIG. 2, gain control block 110 may include components such as, but not limited to, a processor 202 and a filter 204. Additionally, in one particular embodiment, gain may be adjusted automatically. That is, a triggering event such as, for example, a relatively large change in motion, may cause processor to adjust gain accordingly.

Referring again to FIG. 1, probe 102 is shown coupled to ultrasound image processing system 108 via a coupling 114. Additionally, output device 112 is shown coupled to ultrasound image processing system 108 via coupling 116. However, couplings 114 and 116 may comprise any type of coupling such as, but not limited to, a cable, a bus, a wireless coupling, and the like.

In this context, gain refers to a relative increase in signal strength, regardless of origin, such as, but not limited to, an increase in transmission power, amplification, voltage, current, etc. Furthermore, gain may be expressed in a variety of manners such as, but not limited to, decibels (dB). For the purposes of describing the subject matter, gain may be referred to as an adjustment of some or all of the above signals to facilitate generation of an ultrasound image. However, gain of the ultrasound imaging system 108 may refer to: (a) a localized gain that may have an effect on an ultrasound image in predetermined areas, (b) a non-localized gain that may have an effect on an ultrasound image as a whole, and/or (c) any combination thereof.

As previously alluded to, probe 102 is capable of transmitting and receiving ultrasound image signal 104. Accordingly, in FIG. 2, ultrasound image processing system 108 may include a transmit/receive (TX/RX) switch component 206 electrically coupled with probe 102. On the TX side, ultrasound image processing system 108 may include a TX beam forming component 208 electrically coupled with a TX amplifier component 210, which in turn may be electrically coupled to TX/RX switch component 206. On the RX side, TX/RX switch component 206 may be electrically coupled with a RX amplifier component 212. RX amplifier component 212 may be electrically coupled with an analog to digital (A/D) converter component 214, which in turn may be electrically coupled with an RX beam forming component 216. As shown in FIG. 2, ultrasound image processing system 108 may include a beam forming controller component 218 electrically coupled with both TX and RX beam forming components 208 and 214, respectively in this particular embodiment. In the illustrated embodiment of FIG. 2, gain control block 110, including the processor 202 and filter 204, may be electrically coupled with RX beam forming component 216 and various other components of the ultrasound image processing system 108. Gain control block 110 may be implemented as part of a digital signal processing (DSP) system of ultrasound image processing system 108. Additionally, in an alternate embodiment, filter 204 may be included as a component of processor 202. Furthermore, in one particular embodiment, gain control block 110 may include one or more filters.

In FIG. 2, TX/RX switch component 206, TX beam forming component 208, TX amplifier component 210, RX amplifier component 212, A/D converter component 214, RX beam forming component 216, and/or beam forming controller component 218 may comprise any type of components now known or later to be developed as part of an ultrasound image processing system. For example, TX/RX switch component 206 may comprise any type of switching component to facilitate TX/RX to and/or from probe 102. Furthermore, TX/RX switch component 206 may include a multiplexer (MUX). MUX may be utilized to perform a wide range of functions for multiplexing such as, but not limited to, facilitate steering of ultrasound image signal 104, where steering may comprise, for example, utilizing an incident beam of energy directed along a line and sweeping the beam back an forth similar to a radar type sweep across the sky or any other function to facilitate simultaneous transmission and/or receive signals, combine two or more signals into a composite signal and visa-versa, etc. Another example may be that beam forming components 208 and 216 may comprise any type of beam forming components that facilitate beam focusing, such as, for example, delaying channels, and/or any other component employed in analog and/or digital implementations. TX and RX amplifier components 208 and 212 may comprise any variety of amplifier components, for example, RX amplifier component 212 may comprise a time gain compensation (TGC) amplifier, which may facilitate quality control of ultrasound image 113 (shown in FIG. 1).

Continuing with FIG. 2, processor 202 of gain control block 110 may receive, via probe 102, an indication of a rate of change in motion of object 106 (both shown in FIG. 1). Rate of change in motion of an object such as, for example, if fetus moves suddenly or if probe is moved suddenly to a new location may be employed in the particular embodiment to signal a gain adjustment. Any change in motion may also be employed to signal a gain adjustment in alternate embodiments, such as, if an object goes from stationary to motion or goes from steady motion to faster or slower motion. Accordingly, for this particular embodiment, indication may comprise a rate of change in motion. Responsive to the change in motion, processor 202 may adjust a gain for ultrasound image 113 to be provided to output device 112 (both shown in FIG. 1) based, at least in part, on the rate of change in motion of object 106 in this particular embodiment. Furthermore, gain may be adjusted so as to substantially or at least partially correspond to the rate of change in motion of the object 106 in one particular embodiment.

In one particular embodiment, for example, processor 202 may adjust gain by varying coefficients of filter 204. Where, in one particular embodiment, coefficients of filter 204 may be varied to adjust gain in connection with a substantially instantaneous change in motion. For example, coefficients of filter 204 may be varied to adjust the gain corresponding to an average of previously adjusted gains for previous changes in motion, e.g., an average 10 previous adjustments in gain, for example, although claimed subject matter is not limited in scope in these respects.

Accordingly, gain of an ultrasound image processing system may be adjusted based, at least in part, on an amount of change in an image, such as in which relatively small changes in motion of an object may correspond to a relatively small gain adjustment, and relatively large changes in motion of an object may correspond to a relatively larger gain adjustment. Furthermore, in a particular embodiment, a rate at which these gain adjustments may be made may substantially or at least partially correspond to a rate of change in motion of the object, for example, the faster the rate of change in the motion of the object, the faster the rate of gain adjustment, and/or vice-versa.

Filter 204 may comprise a wide variety of filters, such as now known or later developed to be utilized in DSP systems. Accordingly, in one embodiment, filter 204 may be an infinite impulse response (IIR) filter. Alternatively, in one embodiment, filter 204 may be, a finite impulse response (FIR) filter. However, claimed subject matter is not limited in scope in these respects.

FIGS. 1 and 2 illustrated particular embodiments. However, it will also be apparent to one skilled in the art that the embodiments may be practiced without one or more of the described components or including components not specifically described. Furthermore, various components may be omitted and/or simplified. Thus, the described components are merely examples of various components that may be included in a ultrasound image processing system and claimed subject matter is not limited to the particular components or embodiments described.

Figure 3:
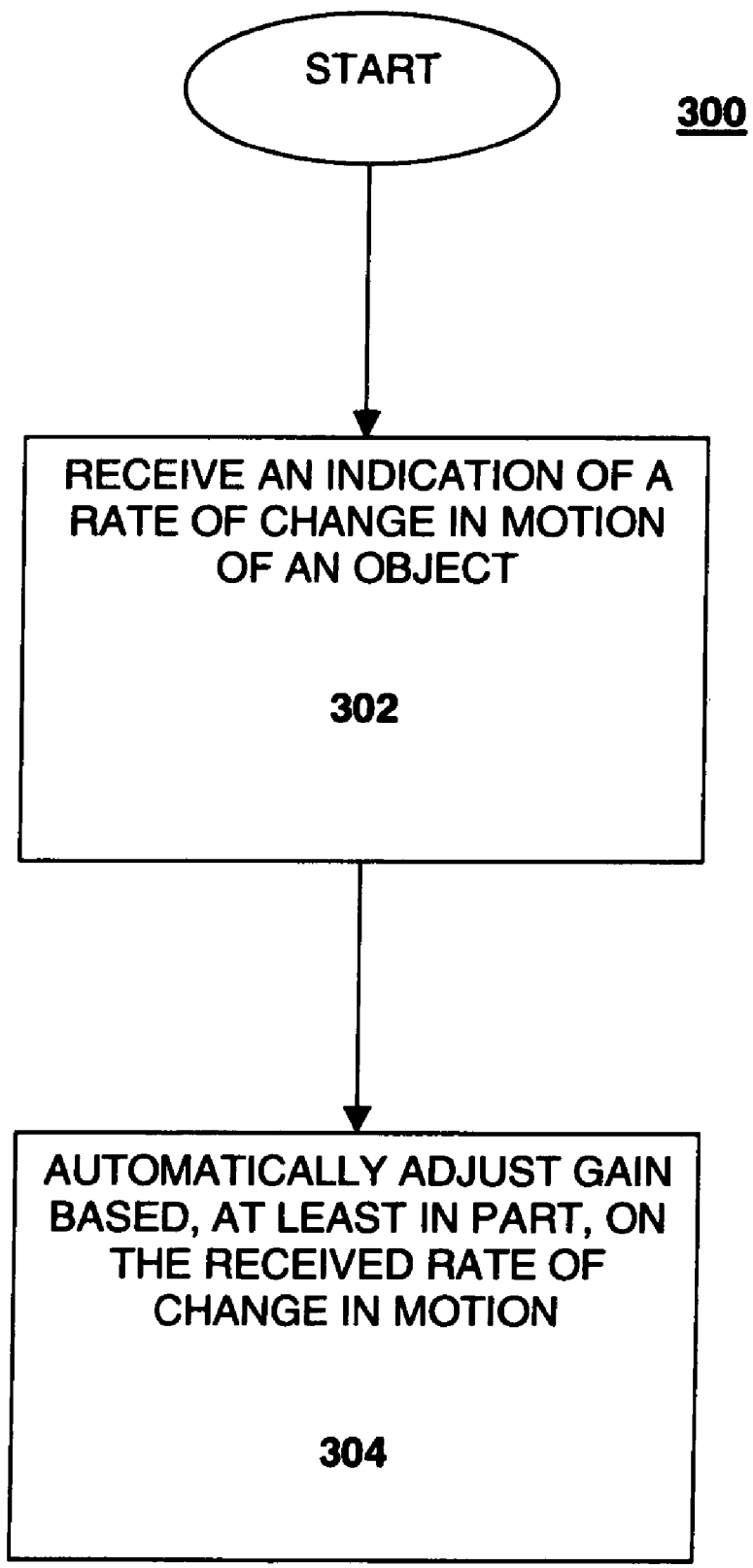
FIG. 3 is a flow chart of an embodiment of a process.

FIG. 3 illustrates a flow chart of an embodiment of a process to adjust a gain. For the illustrated embodiment, gain control block 110 of FIG. 1 may include an implementation of an event driven model for the chart 300. For example, without limitations, gain control block 110 may be designed to be implemented in a system environment where various event notification services are available, although gain control block 110 may include any number of programming approaches and claimed subject matter is not limited to a particular approach.

As illustrated in FIG. 3, an indication of a rate of change in motion of an object may be received, as indicated by block 302 for example. As previously described, for example, rate of change in motion of object 106 may be received via probe 102. In particular, probe 102 may detect the rate of change in motion by transmitting and/or receiving ultrasound image signals 104.

At block 304, a gain is adjusted based, at least in part, on the received rate of change in motion. Gain may be adjusted substantially or at least partially corresponding to the rate of the change in motion of object 106, in a particular embodiment. As previously described, for example, adjustments in gain may be controlled at least in part by processor 202 by variably modifying coefficients of filter 204. As previously described, in one embodiment, the faster the rate of change in the motion of the object, the faster the rate of gain adjustment, and/or vice-versa, although claimed subject matter is not limited in scope in these respects.

Figure 4:
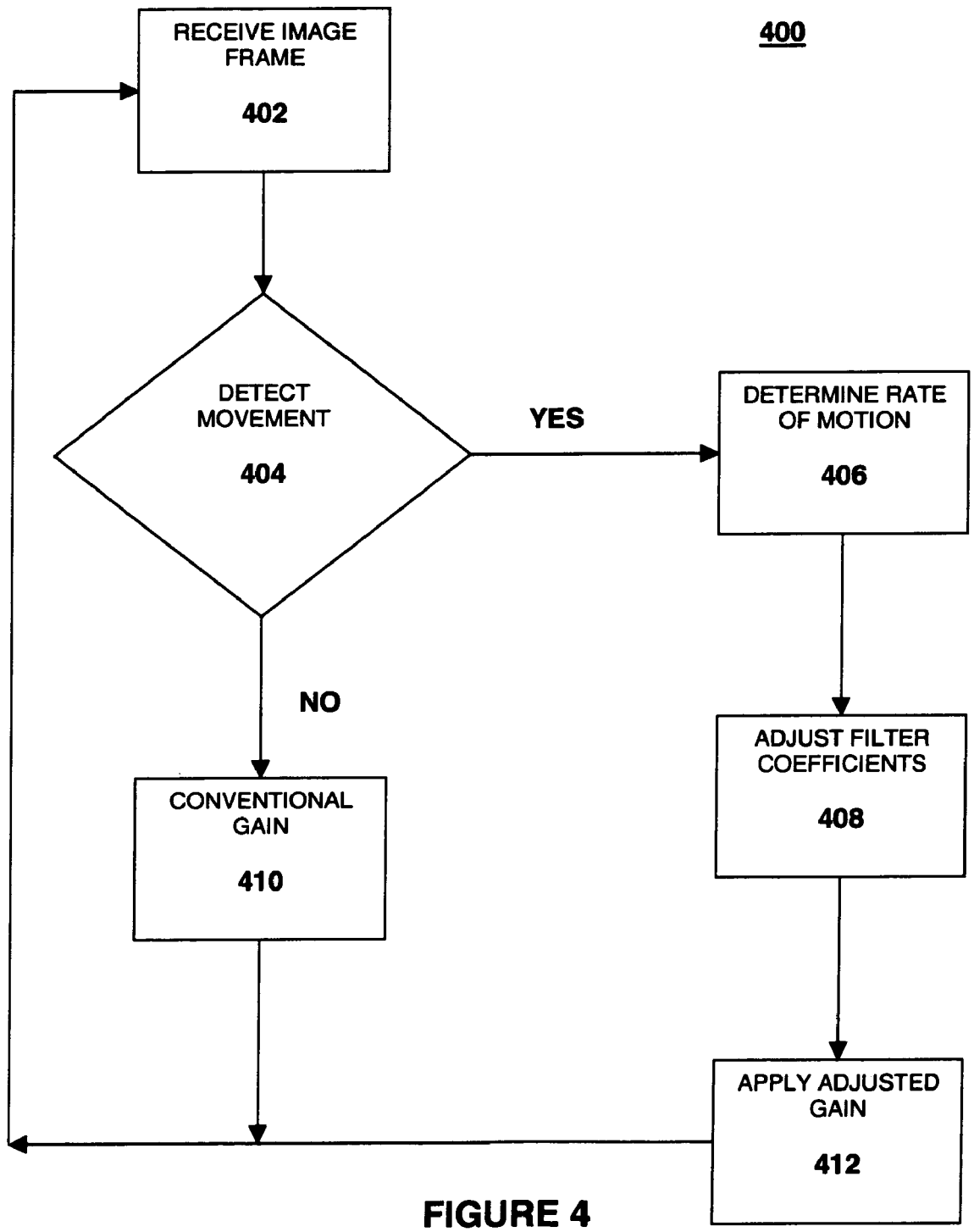
FIG. 4 illustrates a flow chart of another embodiment of a process to adjust a gain.

FIG. 4 illustrates a flow chart of another embodiment of a process to adjust a gain. Here again, for the illustrated embodiment, gain control block 110 of FIG. 1 may include an implementation of an event driven model for the chart 400. For example, without limitations, gain control block 110 may be designed to be implemented in a system environment where various event notification services are available, although gain control block 110 may include any number of programming approaches and claimed subject matter is not limited to a particular approach.

As illustrated in FIG. 4, gain control block 110 receives an image frame, as indicated by block 402 for example. The image frame may comprise, for example, an image frame to be processed for being provided to the output device 112 as the image 113. At block 404, the image frame may be further processed to determine if an indication of a rate of change of motion of an object is received for example. In the particular embodiment, the processing may comprise of segmenting and analyzing the image frame to facilitate detection of motion of an object and its resulting image change for example. If it is determined that an indication of a rate of change of motion of an object is received, a rate of change in motion may be determined at block 406. Then at block 408, as previously described, a gain may be adjusted based at least in part on the rate of change in motion, where for example, the gain may be adjusted at least in part by processor 202 by variably modifying coefficients of filter 204 to at least partially correspond to the rate of change in motion. At block 412, the adjustments in the gain may be applied to an image such as, but not limited to, the image 113 displayed on the output device 112.

In this particular embodiment, for example, if at block 404 if an indication of a rate of change of motion of an object is not received, (i.e., segment and analysis of the image frame does not detect movement and/or change in image of an object), gain control block 110 may provide a gain according to some known or later developed approaches at block 410 and the gain applied accordingly.

FIGS. 5A-5C are graphical representations illustrating at least one example, without limitations, of an adjustment of gain based, at least in part, on a rate of change in motion, where the gain is adjusted at least partially corresponding to the rate of change in motion of an object for one embodiment. For the purposes of illustrating an example, object may comprise of a heart, and in the particular example, the graphical representations may comprise of a sampling of a full cardiac cycle further comprising of 60 image frames. FIG. 5A is a graphical representation of cumulative image frame differences, FIG. 5B is a corresponding graphical representation of a gain determined conventionally, and FIG. 5C is a corresponding graphical representation of adjustment of a gain based, at least in part, on a rate of change in motion, where the gain is adjusted at least partially corresponding to the rate of change in motion of an object.

Referring to FIG. 5B, gain may be determined conventionally by known or later known methods such as, but not limited to, tissue equalization (TEQ) methods. In one embodiment, a gain method such as, but not limited to, TEQ method, may be filtered to produce graphical representation illustrated in FIG. 5C. The relationships between the graphical representations may be calculated, without limitations, as the following relationships.

Cumulative Image Frame:

$$C(k) = \sum_{i}^{N} |B_i(k) - B_i(1)|$$

where sum is over all pixels in an image frame, B is the value 0 or 1 of a pixel in a binary image, and k is the image frame number.

Measure of Overall Gain Adjustment Given by Sum of the Squares of Gain for Each Pixel:

$$G(k) = \sum_{i}^{N} \frac{g_i^2(k)}{N}.$$

Smoothed gain (i.e., adjusting gain) in one particular embodiment utilizing a filter, such as, but not limited to an IIR filter where the location of the pole is adaptive to cumulative differences:

$$s_i(k) = \frac{[g_i(k) + a \cdot s(k-1)]}{(1+a)}$$

where $$a = \frac{(C_0 - C(k))}{C_0}$$

and $C_0$ is a constant.

Accordingly, adjusting gain may be defined by:

$$S(k) = \sum_i^N \frac{s_i^2(k)}{N}.$$

Referring back to FIGS. 5A-5C, graphical representation may be related to the above equations, and for example, FIG. 5A may represent C versus frame number, FIG. 5B may represent G versus frame number, and FIG. 5C may represent S versus frame number.

Figure 6:
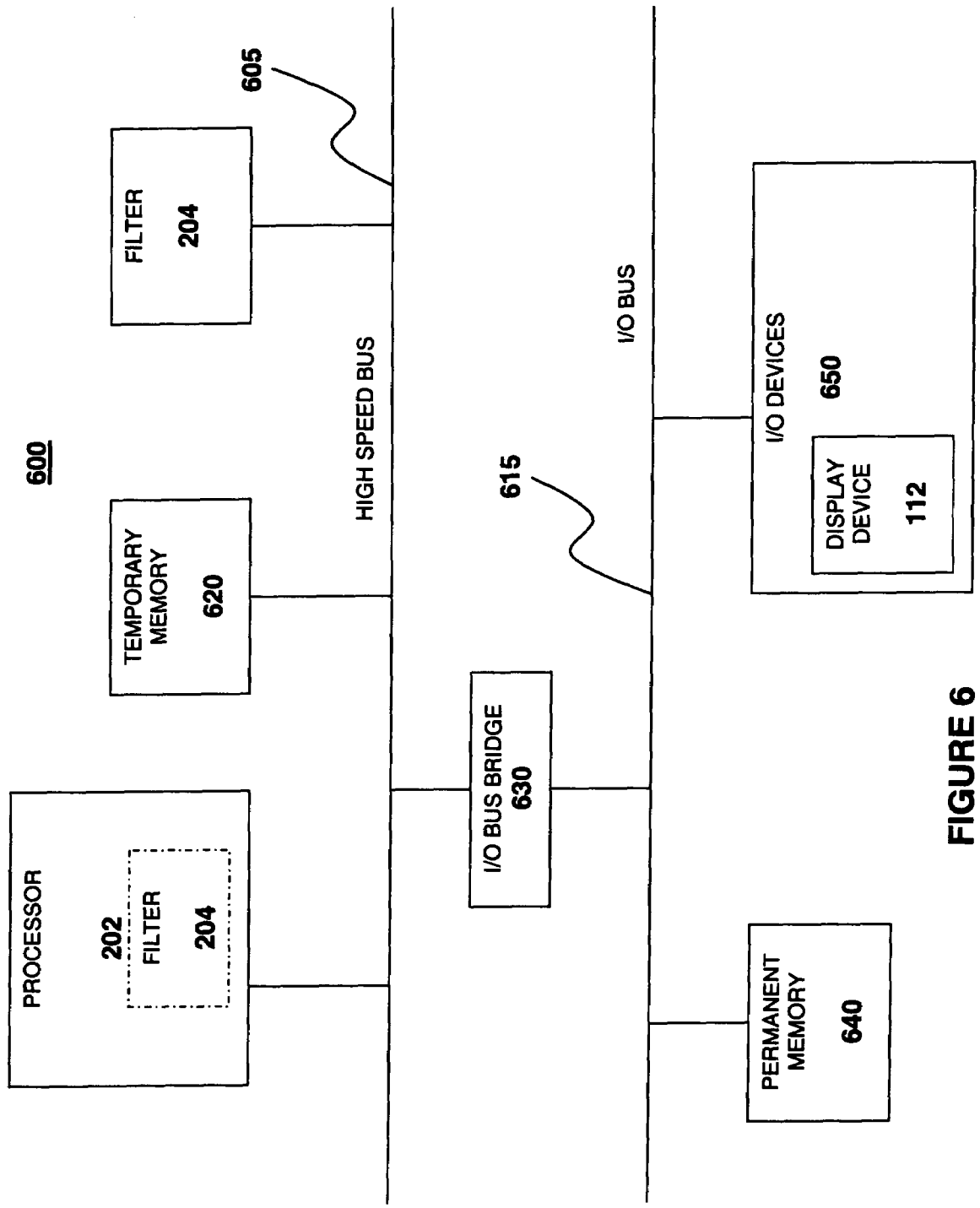
FIG. 6 is a schematic diagram of an embodiment of a generic hardware system.

FIG. 6 illustrates one embodiment of a generic hardware system, although claimed subject matter is not limited in scope in these respects. In the illustrated embodiment, hardware system 600 includes processor 202 which may be coupled to high speed bus 605, which may be coupled to input/output (I/O) bus 615 through bus bridge 630 for example. Temporary memory 620 may be coupled to high speed bus 605. Furthermore, filter 204 may be coupled to high speed bus 605 or as previously alluded to, filter 204 may be included in the processor 202 as part of an instruction set. Permanent memory 640 may be coupled to I/O bus 615. I/O device(s) 650 may also be coupled to bus 615. In one embodiment, the I/O device(s) 650 may include display device 112 (shown in FIG. 1), and/or various other I/O device such as, but not limited to, a keyboard, one or more external network interfaces, etc. As alluded to previously, image data may be stored in permanent memory 640, which may be output to display device 112 or alternatively stored for later retrieval.

Certain embodiments may include additional components, may not require all of the above components, and/or may combine one or more components. For example, temporary memory 620 may be on-chip with processor 202. Alternately, permanent memory 640 may be eliminated and/or temporary memory 620 may be replaced with an electrically erasable programmable read only memory (EEPROM), wherein software routines are executed in place from the EEPROM. Some implementations may employ a single bus, to which all of the components are coupled, while other implementations may include one or more additional buses and/or bus bridges to which various additional components can be coupled. Similarly, a variety of alternate internal networks may be used including, for instance, an internal network based at least in part on a high speed system bus with a memory controller hub and/or an I/O controller hub. Additional components may include additional processors, a CD ROM drive, additional memories, and/or other peripheral components known in the art to be later developed.

Various functions and/or operations, as described above, may be implemented using one or more of a wide range of hardware systems. In one embodiment, functions may be implemented as instructions and/or routines that may be executed by one or more execution units, such as processor 202 for example, within one or more hardware system(s).

These machine executable instructions may be stored using any article accessible medium such as, but not limited to, a machine readable storage medium, including internal memory, such as memories 620 and 640 (shown in FIG. 6), as well as various external and/or remote memories, such as a hard drive, diskette, CD-ROM, magnetic tape, digital video or versatile disk (DVD), laser disk, Flash memory, network server, etc. In one implementation, these software routines may be written in a programming language such as, but not limited to, the C, C+, or C++ programming language. It is to be appreciated, however, that these routines may be implemented in any of a wide variety of programming languages.

In alternate embodiments, various functions and/or operations of the embodiments may be implemented in discrete hardware and/or firmware. For example, one or more application specific integrated circuits (ASICs) may be programmed with one or more of the above-described functions. In another example, one or more functions may be implemented in one or more ASICs on additional circuit boards and/or the circuit boards could be inserted into the system(s) described above. In another example, one or more programmable gate arrays (PGAs) may be used to implement one or more functions and/or operations. In yet another example, a combination of hardware and/or software may be used to implement one or more functions and/or operations.

While there has been illustrated and/or described what are presently considered to be example embodiments of claimed subject matter, it will be understood by those skilled in the art that various other modifications may be made, and/or equivalents may be substituted, without departing from the true scope of claimed subject matter. Additionally, many modifications may be made to adapt a particular situation to the teachings of claimed subject matter without departing from subject matter that is claimed. Therefore, it is intended that the patent not be limited to the particular embodiments disclosed, but that it covers and all embodiments falling within the scope of the appended claims.

What is claimed is:

1. A method for motion adaptive gain comprising:
   receiving an indication of a rate of change in motion of an object, wherein the rate of change in motion comprises a difference in the motion between at least two times;
   adjusting a gain based, at least in part, on said rate of change in motion;
   wherein said gain is adjusted at least partially corresponding to an amount of said rate of change in motion of said object; and
   applying said adjusted gain to an image displayed on an output device.

2. The method of claim 1, wherein said receiving comprises receiving an ultrasound image signal.

3. The method of claim 1, wherein said receiving comprises receiving an analog signal and converting said analog signal to a digital signal.

4. The method of claim 1, wherein said adjusting comprises automatically adjusting a digital signal processing (DSP) system based, at least in part, on a triggering event.

5. The method of claim 1 further comprising:
   receiving an image frame;
   processing said image frame to determine if said indication of said rate of change in motion of said object is received based, at least in part, on said image frame.

6. The method of claim 4, wherein said adjusting comprises varying coefficients of one or more filters.

7. The method of claim 6, wherein said adjusting comprises varying coefficients of one or more infinite impulse response (IIR) filters.

8. A system comprising:
a probe;
an ultrasound image processing system coupled to said probe, said ultrasound image processing system configured to receive an indication of a rate of change in motion of an object, said rate of change in motion comprising a difference in the motion between at least two times, and configured to adjust a gain based, at least in part, on said rate of change in motion, wherein said gain is adjusted at least partially corresponding to an amount of said rate of change in motion of said object; and
an output device coupled to said ultrasound image processing system.

9. The system of claim 8, wherein said probe comprises a transducer.

10. The system of claim 8, wherein said probe comprises a probe is configured to actively scan said object.

11. The system of claim 8, wherein said ultrasound image processing system comprises an ultrasound image processing system is configured to receive an analog signal and configured to convert said analog signal to a digital signal.

12. The system of claim 8, wherein said ultrasound image processing system comprises a gain control block.

13. The system of claim 8, wherein said ultrasound image processing system comprises an ultrasound image processing system configured to receive an image frame, process said image frame to determine if said indication of said rate of change in motion of said object is received based, at least in part, on said image frame, and apply said adjusted gain to an image displayed on said output device.

14. The system of claim 12, wherein said gain control block comprises one or more processors.

15. The system of claim 12, wherein said gain control block comprises one or more filters.

16. The system of claim 15, wherein said one or more filters comprise one or more infinite impulse response (IIR) filters.

17. An apparatus comprising:
a processor;
a computer readable storage medium, coupled to said processor, having stored thereon a plurality of instructions, wherein when executed, the instructions cause the processor to receive an indication of a rate of change in motion of an object, said rate of change in motion comprises a difference in the motion between at least two times, and adjust a gain based, at least in part, on said rate of change in motion, wherein said gain is adjusted at least partially corresponding to said rate of change in motion of said object.

18. The apparatus of claim 17, wherein said instructions cause the processor to receive and an ultrasound image signal.

19. The apparatus of claim 17, wherein said instructions cause the processor to receive an analog signal and convert said analog signal to a digital signal.

20. The apparatus of claim 17, wherein said instructions cause the processor to automatically adjust a digital signal processing (DSP) system based, at least in part, on a triggering event.

21. The apparatus of claim 17, wherein said instructions further cause the processor to receive an image frame, process said image frame to determine if said indication of said rate of change in motion of said object is received based, at least in part, on said image frame, and apply said adjusted gain to an image displayed on an output device.

22. The apparatus of claim 20, wherein said instructions cause the processor to vary coefficients of one or more filters.

23. The apparatus of claim 22, wherein said instructions cause the processor to vary coefficients of one or more infinite impulse response (IIR) filters.

24. An article comprising:
a computer readable medium having stored therein a plurality of instructions, wherein when executed, the instructions cause a processor to receive an indication of a rate of change in motion of an object, said rate of change in motion comprises a difference in the motion between at least two times and adjust a gain based, at least in part, on said rate of change in motion, wherein said gain is adjusted at least partially corresponding to said rate of change in motion of said object.

25. An apparatus comprising:
means for receiving an indication of a rate of change in motion of an object, said rate of change in motion comprises a difference in the motion between at least two times;
means for adjusting a gain based, at least in part, on said rate of change in motion, wherein said gain is adjusted at least partially corresponding to said rate of change in motion of said object; and
means for displaying an ultrasound image having an image quality based at least in part on said adjusted gain.

26. The apparatus of claim 25, wherein said means for receiving comprises means for receiving an ultrasound signal.

27. The apparatus of claim 25, wherein said means for receiving comprises means for receiving an analog signal and converting said analog signal to a digital signal.

28. The apparatus of claim 25, wherein said means for adjusting comprises means for automatically adjusting a digital signal processing (DSP) system based, at least in part, on a triggering event.

29. The apparatus of claim 25, further comprising:
means for receiving an image frame; and
means for processing said image frame to determine if said indication of said rate of change in motion of said object is received based, at least in part, on said image frame.

30. The apparatus of claim 28, wherein said means for adjusting comprise means for varying coefficients of one or more filters.

* * * * *